United States Patent [19]

Zimmerman et al.

[11] Patent Number: 5,362,854

[45] Date of Patent: Nov. 8, 1994

[54] FACTOR VIII COAGULANT POLYPEPTIDES: METHOD OF MAKING

[75] Inventors: Theodore S. Zimmerman; Carol A. Fulcher, both of La Jolla, Calif.

[73] Assignee: Scripps Clinic & Research Foundation, La Jolla, Calif.

[21] Appl. No.: 22,015

[22] Filed: Feb. 24, 1993

Related U.S. Application Data

[60] Division of Ser. No. 730,193, Jul. 15, 1991, Pat. No. 5,214,033, which is a continuation of Ser. No. 232,795, Aug. 16, 1988, abandoned, which is a continuation of Ser. No. 16,214, Feb. 19, 1987, abandoned, which is a continuation of Ser. No. 481,105, Mar. 31, 1983, abandoned.

[51] Int. Cl.⁵ .................... A61K 35/14; C07K 17/02; C07K 3/18

[52] U.S. Cl. ..................... 530/383; 530/413; 435/68.1

[58] Field of Search ................ 530/383, 413; 435/68.1

[56] References Cited

U.S. PATENT DOCUMENTS

| | | | |
|---|---|---|---|
| Re. 32,011 | 10/1985 | Zimmerman et al. | 530/383 |
| 3,631,018 | 12/1971 | Shanbrom et al. | 530/381 |
| 3,652,530 | 3/1972 | Johnson et al. | 530/381 |
| 4,069,216 | 1/1978 | Shanbrom | 530/381 |
| 4,314,997 | 2/1982 | Shanbrom | 424/101 |
| 4,361,509 | 11/1982 | Zimmerman et al. | 530/381 |
| 4,657,894 | 4/1987 | Zimmerman et al. | 530/381 |
| 4,857,635 | 8/1989 | Zimmerman et al. | 530/383 |
| 5,045,455 | 9/1991 | Kuo et al. | 435/69.6 |

FOREIGN PATENT DOCUMENTS

| | | |
|---|---|---|
| 0033578 | 8/1981 | European Pat. Off. . |
| 0033579 | 8/1981 | European Pat. Off. . |
| 0197901 | 10/1986 | European Pat. Off. . |

OTHER PUBLICATIONS

Hoyer et al. *J. Lab. Chem. Md.* 97: 50–64 (1981).
Fay et al. *Proc. Natl. Acad. Sci USA* vol. 79: 7200–7204 (1982).
Nesheim, et al. *J. Biol. Chem* vol 254 (No. 4): 1326–1334 (1979).
Suzuki, et al *J. Biol. Chem.* vol. 257 (No. 11): 6556–6564 (1982).
Vehar et al *Biochemistry* vol. 19 (No. 3): 401–410, (1980).
Burke, et al. *J. Biol. Chem.* vol. 261: 12574–12578 (1986).
Fenton et al. *J. Biol. Chem.* vol. 252: 3587–3598 (1977).
Laura, R. et al. *Biochemistry* vol. 19: 4859–4864 (1980).
Laemmli, U. K. *Nature* vol. 227: 680–685 (1970).
Fairbanks, G. et al. *Biochemistry* vol. 10: 2606–2617 (1971).
Kapitany, R. A. et al. *Analytical Biochemistry* vol. 56: 361–369 (1973).
Knutson, G. J. et al. *Blood* vol. 59, No. 3: 615–624 (Mar. 1982).
Fass, D. N. *Blood* vol. 59, No. 3: 594–600 (Mar. 1982).
Engvall, E. et al. *Immunochemistry* vol. 8: 871–874 (1971).
Johnstone, A. et al. 'Immunochemistry in Practice' Blackwell Scientific Publications, 2nd Ed., pp. 105–109.
Vehar, et al. *Nature* vol. 312: 337–342 (Nov. 22, 1984).
Eaton, et al. *J. Biol. Chem.* vol. 262: 3285–3290, (1987).
Kuo, et al. *Haemostasis* 50: 262 Abstract No. 0818 (1983).

(List continued on next page.)

*Primary Examiner*—Michael G. Wityshyn
*Assistant Examiner*—C. Sayala
*Attorney, Agent, or Firm*—Morgan & Finnegan

[57] ABSTRACT

Fragments of Factor VIII:C polypeptide have been discovered which exhibit highly specific factor VIII activity. Monoclonal antibodies to the polypeptide fragments and methods for the isolation and purification of said fragments are also disclosed.

9 Claims, No Drawings

OTHER PUBLICATIONS

Tuddenham, Edward et al., "The properties of Factor VIII coagulant activity...," vol. 93(1) pp. 40–53, 1979.

Marlar, Richard et al., "Mechanism of Action of Human Activated Protein C...," Blood, vol. 59(5), 1982, pp. 1067–1072.

Horowitz Bernard, et al., "Purification of low molecular weight Factor VIII...," Thrombosis Research, vol. 14, pp. 463–475, 1979.

Levine, James et al., "Thrombin–mediated release of Factor VIII...," Blood, vol. 60(2), pp. 531–534, 1982.

Holmberg, L et al., "Purification of F VIII:C by Antigen–Antibody Chromatography", vol. 12 pp. 667–675, 1978.

Kopitsky, Robert et al., "Thrombin Potentiation of Factor VIII Procoagluant...", Thrombosis & Haemastasis, vol. 47(2), pp. 145–149, 1982.

Fulcher et al., "Characterization of the human factor VIII . . . ", Proc. Natl. Acad. Sci. vol. 79, pp. 1645–1562, Mar. '82.

FACTOR VIII COAGULANT POLYPEPTIDES: METHOD OF MAKING

This invention was made with government support under Grant Number HL 15491 awarded by The National Institutes of Health. The government has certain rights to this invention.

This application is a divisional of U.S. Ser. No. 07/730,193 filed Jul. 15, 1991 which issued to U.S. Pat. No. 5,214,033 on May 25, 1993, which is a continuation of U.S. Ser. No. 07/232,795 filed Aug. 16, 1988, abandoned, which is a continuation of U.S. Ser. No. 07/016,214 filed Feb. 19, 1987, abandoned, which is a continuation of U.S. Ser. No. 06/481,105 filed Mar. 31, 1983 abandoned.

BACKGROUND OF THE INVENTION

This invention relates to new factor VIII polypeptides, that is, proteins, exhibiting coagulant activity. The invention therefore has utility in the therapy for classic hemophilia, and in the further study and characterization of the polypeptide or polypeptide complexes which provide desired clotting behavior to the blood of humans and other mammals.

It has long been known that plasma factor VIII plays a crucial role in blood coagulation, and that thrombin activates the coagulant effect of factor VIII. Recent attempts to characterize factor VIII have postulated that factor VIII is a complex of at least two polypeptides, which are known as VIII:C and VIII:R, and have found coagulant activity to reside in the VIII:C portion. Studies of the effect of thrombin on factor VIII:C have led to the conclusion that thrombin activates this factor by breaking it down into several smaller polypeptides. However, no prior studies have been able to associate thrombin-induced factor VIII activation in humans with any defined polypeptides formed from human factor VIII:C.

For instance, Hoyer and Trabold, in "The effect of thrombin on human factor VIII", J. Lab. Clin. Med. 97:50–64 (1981), sought to purify human factor VIII:C by immunoadsorbent chromatography using a polyclonal antibody to factor VIII:R raised in the rabbit. They then incubated the factor VIII:C with purified human α-thrombin, and determined that small amounts of the thrombin activated the factor VIII:C whereas larger amounts activated it less or not at all. They also concluded that thrombin activation is accompanied by a decrease in the size of the protein, and they proposed a molecular weight of about 116,000 for the activated factor VIII:C. Most significantly, they could not identify specific polypeptides that retained factor VIII:C activity and VIII:CAg determinants.

Fulcher, C. A. and Zimmerman, T. S. in "Characterization of the human factor VIII procoagulant protein with a heterologous precipitating antibody", Proc. Natl. Acad. of Sci. USA, 79:1648–1652 (1982) obtained highly purified human factor VIII:C from plasma concentrate by passing the concentrate through a column containing a monoclonal antibody to factor VIII:R, eluting the VIII:C from the adsorbed VIII:C/VIII:R complex, and concentrating the factor VIII:C on a second column. The purified factor VIII:C was then analyzed by sodium dodecyl sulfate/polyacrylamide gel electrophoresis ("SDS-PAGE"), both before and after addition of thrombin to the purified material. The purified factor VIII:C prior to thrombin addition showed a wide array of bands on sodium dodecyl sulfate-polyacrylamide gel electrophoresis ("SDS-PAGE") corresponding to polypeptides of various molecular weights ($M_r$), including a relatively strong doublet at $M_r$ of 80,000 and 79,000, and at least six additional faintly staining polypeptides with larger $M_r$ including one at $M_r$ about 92,000. Addition of thrombin to the purified factor VIII:C caused the diminution or disappearance of all of the polypeptides shown prior to thrombin addition.

The coagulant activity of the plasma concentrate rose following thrombin addition to a maximum of three times that of the material prior to thrombin addition, and then diminished. The coagulant activity of the purified factor VIII:C also rose to a maximum of three times that of the pre-activated material. That is, the thrombin had essentially the same activating effect on the factor VIII:C in each case. Thus, whereas the purified factor VIII:C possessed a reported specific activity some 3280 times that of the starting material, one skilled in this art would conclude that the increase in specific activity was due to the high degree of purification achieved. There is no basis in this article for ascribing activated coagulant activity to any specific one or more of the large number of polypeptides associated with the bands observed in the purified factor VIII:C prior to activation with thrombin.

SUMMARY OF THE INVENTION

One aspect of the present invention is a factor VIII:C coagulant polypeptide complex characterized in that:

(i) the complex consists of one or more polypeptides which exhibit a band at a point corresponding to an $M_r$ of about 92,000, or bands at points corresponding to $M_r$ values of about 92,000, about 80,000, and about 79,000, or of about 92,000, about 72,000 and about 71,000, when subjected to sodium dodecyl sulfate-polyacrylamide gel electrophoresis in accordance with Procedure A described in the Example hereinbelow;

(ii) the complex exhibits specific coagulant activity higher than that of purified human factor VIII:C which has not been activated by thrombin;

(iii) the complex exhibits the activity in step (ii) over a continuous period of at least about 10 minutes; and (iv) the complex binds to an antibody for human factor VIII:C.

Other aspects of the invention include biological preparations containing the complex, and the treatment of the clotting disorders of hemophilia by administering the complex or preparations thereof. Yet another aspect of the present invention comprises making the complex, or a concentrated preparation thereof, by digesting human factor VIII:C with alpha-thrombin, discontinuing the digestion while the complex described above is present, and concentrating the complex. A further aspect of the invention is a process for recovering VIII:C polypeptides, without losing coagulant activity, from an immunoadsorbent containing monoclonal antibodies to factor VIII:C.

DETAILED DESCRIPTION OF THE INVENTION

As indicated, the present invention encompasses polypeptide complexes which exhibit factor VIII:C coagulant activity and factor VIII:C immunological behavior, and which show characteristic $M_r$ value(s) when analyzed by sodium dodecyl sulfate-polyacrylamide gel electrophoresis (hereafter, "SDS-PAGE"). By "polypeptide complex" is meant not only combinations of two or more polypeptides known to be physically distinct, but also preparations containing only one discernible polypeptide, i.e., that which exhibits a band at an $M_r$ of 92,000.

The description below showing the preparation of the claimed complex utilizes human factor VIII:C which has been highly purified, in order to free the identification and characterization of the novel product from the effects of extraneous polypeptides. It should be recognized, though, that the invention itself is not dependent on how the starting material has previously been treated, except where specifically indicated. The active factor VIII:C polypeptides of the present invention can be prepared not only by thrombin digestion as described in greater detail below, but also by recombinant DNA techniques in which the polypeptides of interest are produced by bacteria, yeast, or other cells into which one or more genes for producing the polypeptides of interest are inserted by techniques known to those of ordinary skill in the art. Either process for producing the complex of interest can be expected to produce the complex in a mixture with one or more other polypeptides.

Any plasma or plasma concentrate containing human factor VIII:C can be employed to advantage. The novel coagulant polypeptide complex can be prepared from human factor VIII:C which has been ultrapurified in accordance with the process described in U.S. Pat. No. 4,361,509, issued Nov. 30, 1982, the disclosure of which is hereby incorporated herein by reference. In that process, a source of factor VIII:C such as plasma or a plasma concentrate is passed through an immunoadsorbent column to which monoclonal antibodies to factor VIII:R have been attached. The factor VIII:R/VIII:C complex is adsorbed on the column, and then the factor VIII:C is eluted and passed through a second column such as aminohexyl agarose. It should be noted that the second column can also be an immunoadsorbent containing antibodies to factor VIII:C. The factor VIII:C should be kept free of $\alpha$-thrombin and other similarly acting proteases. The factor VIII:C is conveniently stored in a saline, buffered solution containing, e.g., 0.3M calcium chloride, at a pH of about 6.8 to about 7.4.

The human factor VIII:C is then digested with $\alpha$-thrombin under conditions effective to form the polypeptide complex described below. The purified $\alpha$-thrombin can be prepared by the procedure described by Fenton, J. W. II; Fasco, M. J.; Stackrow, A. B.; Aronson, D. L.; Young, A. M.; and Finlayson, J. S. "Human Thrombin. Production, Evaluation, and Properties of $\alpha$-Thrombin". J. Biol. Chem. 252: 3587-3598 (1977).

The $\alpha$-thrombin and the factor VIII:C are combined in an aqueous system, preferably buffered at a pH of about 6.8 to about 7.4. The thrombin should be present in an amount relative to the factor VIII:C that is sufficient to permit reaction with the factor VIII:C, but not so high that the factor VIII:C degrades to inactive polypeptides before the desired active polypeptide complex can be recovered. As an illustration, a preparation containing 200-400 units (0.2 mg/ml) of factor VIII:C per ml should be digested with about 0.1 to about 0.5 units/ml of $\alpha$-thrombin. The digestion can proceed at room temperature; too high a temperature can denature the polypeptides, and too low a temperature can retard the progress of the digestion.

The digestion is allowed to proceed for a time long enough to permit the formation of the desired polypeptide complex. The optimum time will be from 0.1 to about 60 minutes, with times from 0.1 to 30 minutes preferred. Times from 1 to 10 minutes have been found highly satisfactory, although it will be recognized that optimum times can be identified with minimal experimentation using aliquots of the factor VIII:C starting material being treated. An optimum time is that which forms the maximal amount of the polypeptide complex exhibiting an $M_r$ of about 92,000, accompanied by the formation of a protein complex exhibiting an $M_r$ doublet of about 79,000 and about 80,000, without degrading the $M_r$ 92,000 polypeptide significantly. It appears that the $M_r$ 79,000-80,000 doublet can function after it has undergone degradation to a complex exhibiting a doublet at $M_r$ values of 71,000-72,000. However, the 71,000-72,000 doublet is associated with loss of factor VIII:C activity.

The digestion is then discontinued by adding to the reaction mixture an effective amount of (p-amidinophenyl) methanesulfonyl fluoride (hereafter, "p-AMPSF"). The p-APMSF prevents the $\alpha$-thrombin from reacting further with the factor VIII:C proteins, without itself degrading those proteins. The amount of p-APMSF to add should comprise about 1.5 to about 2.5 millimoles per unit of $\alpha$-thrombin activity initially present in the reaction mixture.

p-APMSF can be obtained through Cal-Med Company, San Francisco, Calif., and its preparation is described in Laura, R.; Robinson, D. J.; and Bing, D. H. "(p-Amidinophenyl)methanesulfonyl Fluoride, an Irreversible Inhibitor of Serine Proteases", Biochemistry (1980) 19, 4859-4864, at 4861.

The reaction mixture is then treated to concentrate the polypeptide complex comprising the present invention. Preferably, the polypeptide complex is concentrated with respect to other factor VIII and non-factor VIII proteinaceous material, to provide the complex in a form which affords the very high activity possessed by the complex in the purified form. Purification techniques include, for example, ultrafiltration, ultracentrifugation, ion exchange, gel permeation chromatography, preparative electrophoresis, isoelectric focusing, and gel and affinity chromatography.

The desired complex can also be concentrated and/or recovered by passing the reaction mixture, which can already have been concentrated by another technique, through an immunoadsorbent column containing anti-human VIII:C antibodies attached to agarose (see the Example below). The active VIII:C complex adsorbs preferentially to the column, and is then eluted from the column with a solution of calcium ions (e.g., $CaCl_2$) and a non-ionic surfactant. Suitable non-ionic surfactants include alkyl phenyl polyoxyethylenes such as Triton-X-100, -N-101, or -X-405 (Eastman Chemical Co.); Tween-20, -60 or -80 (Sigma Chemical Co.); and Nonidet P-40 (Sigma Chemical Co.); all of these are well-known articles of commerce having known chemical formulas.

The amounts of calcium ion and surfactant to use should be high enough to desorb the polypeptide complex, but not so high that the eluant degrades the polypeptide. A calcium ion concentration of up to about 0.5M is satisfactory, and 0.25M is preferred. A surfactant concentration of up to about 1 wt. % is satisfactory, and about 0.1 wt. % is preferred. The eluant is applied to the immunoadsorbent column at about 1 to about 8 bed volumes per hour, and preferably about 3 to about 4 per hour. Too high a flow rate risks disruption of the column and denaturation of the polypeptide complex. The skilled practitioner will readily adapt these guidelines to immunoadsorbent processes other than fixed-bed columns.

The VIII:C polypeptide complex is recovered in a suitable buffer, at a pH of about 6.8 to 7.4, which also contains calcium ion and surfactant from the eluant solution. The calcium and surfactant concentrations can be lowered, and the surfactant preferably removed, by dialyzing the solution against a buffer such as the VIII:C buffer used in the Example which contains a lower amount of calcium ion. The complex of this invention can be stored in this solution, or lyophilized. The complex can be administered to patients with hemophilic clotting disorders by adjusting the calcium content to be physiologically compatible and injecting a sterile solution thereof.

When analyzed by SDS-PAGE as shown below, the complex of this invention exhibits an $M_r$ of about 92,000, and can normally contain material exhibiting an $M_r$ doublet of about 79,000 and about 80,000, which can have undergone degradation to exhibit an $M_r$ doublet of about 71,000 and about 72,000. In its purified form, this band or the group of three bands are essentially the only bands that appear. However, it will be appreciated that the present invention also encompasses biological preparations in which less than 100%, i.e., 95%, 90%, or even 80%, 70% or 60%, or even as little as 20%, 10%, or 1% of the proteinaceous matter present comprises the complex of the present invention. This invention thus encompasses preparations in which the factor VIII:C activity is due to the presence of the complex.

The protein complex of the present invention possesses specific VIII:C coagulant activity higher than that exhibited by purified human factor VIII:C, for instance human factor VIII:C purified by the process disclosed and claimed in the aforementioned U.S. Pat. No. 4,361,509. Indeed, the activity of the purified complex should be several times, e.g., 3 to 5 times, that of purified human factor VIII:C, and is advantageously at least 10 times or even 50 times as active. Likewise, biological preparations comprising the complex of this invention in association with one or more other proteins can be prepared which exhibit higher specific activity than that afforded in previously known coagulant preparations. The complex of the present invention is further characterized in that its specific activity cannot be increased further to any significant extent (e.g., by a factor less than 3, if at all) by digestion with α-thrombin. Preferably, the specific activity of the invention preparations exceeds that of purified human factor VIII:C by a factor of 3 to 5, and more advantageous by at least 10 times, by 50, or even by 100 times.

The protein complex of the present invention, and biological preparations thereof, are characterized in that the enhanced activity described above remains present over a continuous period of at least about 10 minutes and preferably at least about 30 minutes. Of course, activity will generally be stable for much longer. The complex also possesses the immunological characteristics of a factor VIII:C protein, i.e., it binds to an antibody for human factor VIII:C. This can be ascertained, for instance, by growing a monoclonal antibody to factor VIII:C as described below, attaching the antibody to an agarose column, passing an aqueous solution of the complex through the column, and assaying the resultant solution for factor VIII:C activity.

EXAMPLE

This Example shows how factor VIII:C was purified from commercial concentrate and digested with purified α-thrombin. A monoclonal antibody to factor VIII:C was produced and used to identify VIII:C polypeptides. At several selected points during the digestion, portions of the digestion mixture were assayed for VIII:C (coagulant) activity, and for protein bands using SDS-PAGE.

Purification of VIII:C

All steps were at room temperature. Chemicals were reagent grade. 20 bottles of commercial factor VIII concentrate (provided by Armour Pharmaceutical) were reconstituted in 500 ml of VIII:C buffer (0.02M imidazole/0.15M sodium chloride/0.1M L-lysine HCl/0.02% sodium azide, pH 6.8). This sample, which contained a total of 17,000 units of VIII:C activity, was applied to an immunoadsorbent column. The column was cyanogen bromide-activated agarose (Sepharose 4B, Pharmacia, Piscataway, N.J.), to which monoclonal antibodies to VIII:R had been covalently bonded. The antibodies were raised and attached to the column as described in the aforementioned U.S. Pat. No. 4,361,509. The antibodies were precipitated from ascites fluid using 50% ammonium sulfate, reprecipitated two more times, and then attached to the column at a density of 2–4 mg/ml of Sepharose. The immunoadsorbent was pre-eluted with 3M sodium thiocyanate, washed with VIII:C buffer (0.02M imidazole HCl pH 7.0, 0.15M NaCl, 0.1M L-lysine-HCl, 0.02% sodium azide), treated twice with 2 mM di-isopropyl fluorophosphate, and then the concentrate was added.

The column was washed with 20 liters of VIII:C buffer containing 0.15M sodium chloride, and VIII:C was then eluted from the VIII:R with VIII:C buffer containing 0.25M calcium chloride. Active fractions were pooled and concentrated under nitrogen pressure 100-fold in an Amicon stirred cell with a YM10 membrane. The concentrate was then diluted 1:10 in VIII:C buffer and applied to a 4 ml column of aminohexyl-Sepharose (Pharmacia) equilibrated in VIII:C buffer containing 0.025M calcium chloride, VIII:C was eluted in high concentration with VIII:C buffer containing 0.3M calcium chloride at a flow rate of 10 ml/hr. The concentrated immunoadsorbent pool was adjusted to 0.25M calcium chloride and adsorbed twice for 1 h each time with 1/10 vol/vol of a mixture of monoclonal anti-fibrinogen, anti-fibronectin and anti-vWF antibodies which had been coupled to cyanogen bromide-activated Sepharose.

SDS-PAGE "Procedure A"

Discontinuous SDS polyacrylamide slab gel electrophoresis was performed based on the procedure of Laemmli, U.K., Nature 227, 680–685, 1970. The "Procedure A" followed is:

I. Sample Preparation
1. Dialyze the protein sample (ideally 50–100 microliters containing 5–60 micrograms of protein) against sample buffer overnight at room temperature. If the sample contains calcium ion, include 10 millimolar ethylenediamine tetracetic acid (EDTA) in the sample buffer.
2. Place the dialyzed sample in a tube and add 1/10 volume of 10% SDS. Cover the tube with aluminum foil. Heat the sample in a boiling waterbath for 10 minutes.

3. Remove the sample from the waterbath and add to it 1/10 volume of 500 millimolar dithiothreitol. Incubate it at 56° C. for 4 hours.
4. Allow the sample to cool to room temperature and prepare it for layering onto the gel by adding stock glycerol solution to 10% final concentration and stock bromophenol blue dye solution to 0.05% final concentration.

II. Preparation of gel solutions (use deionized, distilled water)
1. Stock glycerol solution: 50% glycerol
2. Stock bromophenol blue dye solution: 0.5% bromophenol blue
3. Lower gel stock solution:
   18.2 grams of Tris base
   4 ml of 10% SDS
   final volume 100 ml.
   Adjust pH to 8.8 with concentrated hydrochloric acid. Filter.
4. Upper gel stock solution:
   6.1 grams of Tris base
   4 ml of 10% SDS
   Final volume 100 ml
   Adjust pH to 6.8 with concentrated hydrochloric acid. Filter.
5. Sample buffer
   0.01M sodium phosphate
   1.0% SDS
   10 millimolar disodium EDTA
   Final volume 1 liter
   pH adjusted to 7.0 with sodium hydroxide or phosphoric acid.
6. Acrylamide stock solution:
   Dissolve 30 g of acrylamide in 50 ml of water and add 0.8 g of bisacrylamide. Bring to 100 ml final volume. Filter the solution and store in the dark at 4° C.
7. Stock electrode buffer solution:
   30.3 g Tris base
   144.1 g glycine
   final volume 1 liter
8. Electrode buffer
   100 ml of stock electrode buffer solution
   890 ml water
   10 ml of 10% SDS
9. Stock Coomassie blue dye solution
   1% Coomassie blue R 250 in water
   Dissolve with stirring for at least 30 minutes at room temperature and filter.
10. Ammonium persulfate solution
    10% ammonium persulfate.
    Stored in dark at 4° C. and made fresh every week.

III. Gel Preparation and Running: Final acrylamide concentration=7.5%
1. Lower gel solution

| 20 ml of lower gel | |
|---|---|
| Stock lower gel solution | 5 ml |
| Stock acrylamide solution | 5 ml |
| Water | 10 ml |
| N,N,N',N'-tetramethylethylenediamine (TEMED) | .005 ml |
| 10% ammonium persulfate | 0.1 ml |

2. Upper gel solution

| 10 ml of upper gel | |
|---|---|
| Stock upper gel solution | 2.5 ml |
| Stock acrylamide solution | 1.0 ml |
| Water | 6.5 ml |
| N,N,N',N'-tetramethylethylenediamine (TEMED) | 0.01 ml |
| 10% ammonium persulfate | 0.03 ml |

3. Procedure:
   a. Prepare the slab gel apparatus for a 14.5 cm×9.0 cm×0.8 mm slab gel. The apparatus is a standard gel electrophoresis apparatus, available, for instance, from Hoeffer Scientific Instruments, San Francisco, Calif.
   b. Mix all lower gel ingredients except the TEMED and ammonium persulfate in a 50 ml vacuum flask and de-aerate. Then add the TEMED and ammonium persulfate, mix gently and pour the lower gel immediately. Layer the lower gel with water-saturated butanol and allow it to polymerize undisturbed for at least 1 hour.
   c. Pour off the butanol layer and rinse the top of the lower gel with the complete upper gel mixture. (The upper gel mixture is prepared, de-aerated and TEMED and ammonium persulfate are added as for the lower gel above).
   d. Pour the upper gel and insert the comb into the upper gel allowing at least 1.0 cm between the bottom of the comb teeth and the upper gel-lower gel interface. Fill with upper gel solution as full as possible. Allow upper gel to polymerize at least 1 hour before running the gel.
   e. To remove the comb, pipet electrode buffer over the top of the upper gel and gently remove the comb. Rinse the upper gel wells with electrode buffer several times.
   f. Assemble the apparatus for running and add electrode buffer. Apply the sample(s) by layering it into the upper gel wells underneath the buffer layer.
   g. Run the gel using constant current: 8 milliamperes while samples are in the upper gel and 15 milliamperes while samples are in the lower gel. Stop the electrophoresis when the bromophenol blue dye front is 1.0 cm from the bottom of the lower gel.

IV. Fixing and Staining the gel
Reference: Fairbanks, G., Steck, T. L., and Wallach, D. F. N., Biochemistry 10, 2606-2617, 1971.
1. Fix the gel at least overnight in a sealed chamber in a solution containing 25% isopropanol, 10% acetic acid, 10 ml of 1% Coomassie blue stock solution, final volume 400 ml.
2. Next, soak the gel at least 1 hour in 10% isopropanol, 10% acetic acid and 1.0 ml of 1% Coomassie blue stock solution, final volume 400 ml.
3. Soak the gel about 4 hours in 10% acetic acid with changes or until completely destained.
4. The destained gel can be dried onto filter paper using a gel dryer to increase contrast.

Approximately 5-20 g of protein was applied to the gels. VIII:C $M_r$s were calculated for reduced samples by semilogarithmic plots of $M_r$ versus migration distance, using reduced fibronectin ($M_r$ 200,000), phosphorylase b ($M_r$ 95,000), bovine serum albumin ($M_r$ 68,000), and IgG heavy chain ($M_r$ 50,000) as standards.

Scanning and integration of a photographic print of the finished gel was done using a Zeineh soft laser scanning densitometer. Periodic acid-Schiff staining was by the method of Kapitany and Zebrowski, "A high-resolution PAS stain for polyacrylamide gel electrophoresis". Anal. Biochem. 56: 361–369 (1973).

Production of monoclonal antibody against VIII:C

Monoclonal antibodies were produced as described in U.S. Pat. No. 4,361,509 using purified VIII:C as immunogen. The antibodies were selected with a solid-phase assay in Linbro-Titertek (Flow Laboratories, Inglewood, Calif.) plates and an enzyme-linked immunoadsorbent (ELISA) detection system described in Engvall, E. and Perlmann, P. "Enzyme-linked immunoadsorbent assay (ELISA), Quantitative assay of immunoglobulin G" Immunochemistry 8:871–874 (1971)) using a peroxidase-antibody conjugate (Zymed Laboratories, Burlingame, Calif.). The plates were coated with 100 ng of purified VIII:C per well. The ELISA-positive culture supernatant of the clone selected for use in this study also inhibited plasma VIII:C activity. The VIII:C inhibitory activity of the monoclonal anti-VIII:C antibody purified from ascites fluid was 15 Bethesda units per mg of protein.

Thrombin activation time course analysis of purified VIII:C.

Purified human α-thrombin (sp. act. 2534 U/mg, final concentration 0.5 U/ml), was added to the purified VIII:C (final concentration 167 ug/ml) in imidazole saline buffer containing 0.04M $CaCl_2$. Buffer alone was added to a control aliquot. The solutions were incubated at room temperature and at various time intervals samples of the VIII:C-thrombin mixture were added to tubes containing p-APMSF (Cal-Med, San Francisco, Calif.) to inactivate the thrombin rapidly and irreversibly. In order to minimize hydrolysis of p-APMSF, it was diluted 1:10 from a stock solution (100 mM in methanol) into imidazole saline buffer 60 seconds before reaction with the VIII:C-thrombin samples. The final p-APMSF concentration was 1 mM. The control aliquot was treated similarly with p-APMSF at the start of the experiment. At the end of the 60 minute time course, all VIII:C samples were assayed for VIII:C activity using an activated partial thromboplastin time assay described in the literature and then prepared for SDS-PAGE.

Results

The specific activity of the purified factor VIII:C was 2000 units/mg. Thrombin activation of purified VIII:C activity was analyzed over a 60 minute time course. Before thrombin exposure the untreated VIII:C sample showed the characteristic array of VIII:C forms ranging from a doublet at $M_r=79{,}000$–$80{,}000$ to a band at $M_r=188{,}000$. A band above $M_r=188{,}000$ and two bands below $M_r=79{,}000$ did not bind to the monoclonal anti-VIII:C antibody immunoadsorbent. The bands between $M_r=79{,}000$ and $M_r=188{,}000$ did bind to the anti-VIII:C antibody.

During the first 5 minutes of the thrombin activation time course, all but one of the monoclonal anti-VIII:C antibody reactive bands with an $M_r$ greater than 92,000 gradually disappeared and were undetectable when VIII:C activity reached its peak at 5 minutes.

A band at $M_r=122{,}000$ appeared thrombin-resistant in only some experiments, but after extensive thrombin treatment neither this band nor any other band was reactive with the immobilized monoclonal anti-VIII:C antibody.

A band at $M_r=92{,}000$ increased in intensity as VIII:C activity decreased. A doublet at $M_r=79{,}000$ and 80,000 appeared to be converted to a doublet at $M_r=71{,}000$–$72{,}000$, with the latter form predominant from 5 to 60 min. as VIII:C activity decreased. Two bands, at $M_r=54{,}000$ and $M_r=44{,}000$, became clearly visible from 5 to 60 min. The $M_r=44{,}000$ band also appeared as a doublet in some experiments. The $M_r=71{,}000$–$72{,}000$ doublet, the $M_r=54{,}000$ band and the $M_r=44{,}000$ band were not removed to a significant degree by the immobilized monoclonal anti-VIII:C antibody.

Scanning and integration of the gel discussed above allowed correlation of changes in polypeptide concentration with changes in VIII:C activity. The results are shown in the Table. As shown, the $M_r=92{,}000$ band increased and then decreased in concentration in parallel with VIII:C activity. This suggests that the $M_r=92{,}000$ band is an active form of VIII:C whose concentration increased in the thrombin digestion. The $M_r=54{,}000$ and $M_r=44{,}000$ bands increased steadily in concentration between 1 and 40 min., even after activity of the mixture declined.

Most of the $M_r=79{,}000$–$80{,}000$ doublet was lost during the first 0.1 to 10 min. as VIII:C activity peaked, while most of the $M_r=71{,}000$–$72{,}000$ doublet appeared during this time and predominated even as VIII:C activity decreased. These data suggest that the $M_r=71{,}000$–$72{,}000$ doublet was derived from the $M_r=79{,}000$–$80{,}000$ doublet and that the $M_r=71{,}000$–$72{,}000$ doublet is inactive by itself. These data also suggest that the $M_r=71{,}000$–$72{,}000$ doublet retains the ability to complex with the $M_r=92{,}000$ polypeptide and this complex would also have activity.

Direct evidence that the $M_r=92{,}000$ polypeptide is complexed with the $M_r=79{,}000$–$80{,}000$ doublet derives from experiments utilizing the anti-VIII:C monoclonal immunoadsorbent. It was first shown that the monoclonal antibody reacts predominantly with the $M_r=79{,}000$–$80{,}000$ doublet and not with the $M_r=92{,}000$ polypeptide. This was shown by electrophoretic transfer experiments. Then it was shown that the monoclonal anti-immunoadsorbent removed both the $M_r=79{,}000$–$80{,}000$ doublet and the $M_r$ 92,000 polypeptide from the solution. The $M_r=79{,}000$–$80{,}000$ doublet and the $M_r=92{,}000$ polypeptide could be eluted from the immunoadsorbent column with 10 mM EDTA, whereas the doublet remained bound. The doublet could be subsequently eluted with 3M sodium thiocyanate. These experiments demonstrated that the $M_r$ 92,000 polypeptide bound to the immunoadsorbent because it was complexed with the $M_r$ 79,000–80,000 doublet and that it was this doublet which bound directly to the immunoadsorbent.

| Time (min) from addition of thrombin to addition of p-APMSF: | 0* | 0.1 | 1 | 2 | 5 | 10 | 20 | 30 | 40 | 60 |
|---|---|---|---|---|---|---|---|---|---|---|
| Activity of digestion mixture | 300 | 900 | 1300 | 1350 | 1400 | 1250 | 800 | 375 | 250 | 100 |

Amount of each poly-

-continued

| Time (min) from addition of thrombin to addition of p-APMSF: | 0* | 0.1 | 1 | 2 | 5 | 10 | 20 | 30 | 40 | 60 |
|---|---|---|---|---|---|---|---|---|---|---|
| Activity of digestion mixture | 300 | 900 | 1300 | 1350 | 1400 | 1250 | 800 | 375 | 250 | 100 |

| peptide ($M_r$) present, as % of total protein present: | | | | | | | | | | |
|---|---|---|---|---|---|---|---|---|---|---|
| $M_r = 92{,}000$ | 7.3 | 9.5 | 11.1 | 11.5 | 11.8 | 9.6 | 7.3 | 6.7 | 4.9 | 4.4 |
| $M_r = 79{-}80{,}000$ | 21.9 | 18.8 | 16.1 | 12.9 | 11.0 | 8.4 | 9.0 | 8.6 | 7.4 | 7.4 |
| $M_r = 71{-}72{,}000$ | 0.0 | 9.0 | 11.2 | 12.9 | 16.5 | 15.9 | 15.7 | 18.8 | 18.2 | 20.4 |
| $M_r = 54{,}000$ | 4.9 | 5.9 | 5.1 | 5.7 | 7.1 | 9.4 | 10.2 | 11.8 | 13.7 | 13.5 |
| $M_r = 44{,}000$ | 0.0 | 0.0 | 0.0 | 3.1 | 3.7 | 5.9 | 6.1 | 7.2 | 7.8 | 7.6 |

*Measurements just prior to addition of α-thrombin
Activity is in Factor VIII:C Bethesda units/ml

What is claimed is:

1. The process of making a biological preparation having enhanced Factor VIII:C coagulant activity, comprising the steps of
   (a) digesting human Factor VIII:C in a digestion mixture with an effective amount of α-thrombin under digestion conditions to form a Factor VIII:C polypeptide complex in association with one or more other polypeptides;
      (i) the complex comprising a polypeptide which exhibits a band at a point corresponding to an M, value of about 92,000, and at least one polypeptide which exhibits a band at a point corresponding to an M, value selected from the group consisting of about 80,000, about 79,000, about 72,000, and about 71,000, when subjected to sodium dodecyl sulfate-polyacrylamide gel electrophoresis;
   (b) discontinuing the digestion of step (a) while said polypeptide complex is still present in said digestion mixture; and
   (c) optionally, concentrating the complex, so that said complex comprises at least about 1 wt % of the proteinaceous matter in the preparation.

2. The process of claim 1 wherein in step (c) the complex comprises at least about 60% by weight of the proteinaceous matter in the preparation.

3. The process of claim 1 wherein the human Factor VIII:C has previously been purified.

4. The process of claim 1 wherein in step (c) the complex is concentrated by
   adsorbing said complex from the mixture onto an immunoadsorbent containing a monoclonal antibody specific to human Factor VIII:C,
   eluting the mixture depleted in said complex from the particles, and then
   eluting the complex from an immunoadsorbent with an aqueous solution containing calcium ions and a nonionic surfactant under elution conditions effective to desorb the complex from the immunoadsorbent without denaturing the polypeptides in the complex.

5. The process of claim 4 wherein the solution contains up to about 0.5M of calcium ion and up to about 1 wt. % of surfactant, and the solution is applied to the immunoadsorbent at up to about 8 bed volumes per hour.

6. A process for recovering a Factor VIII:C coagulant polypeptide complex in active form from an immunoadsorbent, containing a monoclonal antibody to human Factor VIII:C to which the complex is adsorbed, the complex characterized in that:
   (i) the complex comprises a polypeptide which exhibits a band at a point corresponding to an M, value of about 92,000, and at least one polypeptide which exhibits a band at a point corresponding to an M, value selected from the group consisting of about 80,000, about 79,000, about 72,000, and about 71,000, when subjected to sodium dodecyl sulfate-polyacrylamide gel electrophoresis;
   the process comprising eluting the complex from the immunoadsorbent with an aqueous solution containing calcium ions and a nonionic surfactant under elution conditions effective to desorb the complex from the immunoadsorbent without denaturing the polypeptides in the complex.

7. The process of claim 6 wherein the solution contains up to about 0.5M of calcium ion and up to about 1 wt. % of surfactant, and the solution is applied to the immunoadsorbent at up to about 8 bed volumes per hour.

8. A process for recovering a Factor VIII:C coagulant polypeptide complex in active form from a source comprising a mixture of said complex and one or more other polypeptides,
   the complex comprising a polypeptide which exhibits a band at a point corresponding to an M, value of about 92,000, and at least one polypeptide which exhibits a band at a point corresponding to an M, value selected from the group consisting of about 80,000, about 79,000, about 72,000, and about 71,000, when subjected to sodium dodecyl sulfate-polyacrylamide gel electrophoresis;
   the process comprising;
   adsorbing said complex from said source onto an immunoadsorbent containing a monoclonal antibody specific to human Factor VIII:C;
   eluting the source depleted in said complex from the immunoadsorbent, and then
   eluting the complex from the immunoadsorbent with an aqueous solution containing calcium ions and a nonionic surfactant under elution conditions effective to desorb the complex from the immunoadsorbent without denaturing the polypeptides in the complex.

9. The process of claim 8 wherein the solution contains up to about 0.5M of calcium ion and up to about 1 wt. % of surfactant, and the solution is applied to the immunoadsorbent at up to about 8 bed volumes per hour.

* * * * *